(12) United States Patent
Chen

(10) Patent No.: US 9,783,498 B2
(45) Date of Patent: Oct. 10, 2017

(54) PROCESS FOR PREPARING THE ANTI-TUMOR AGENT 6-(7-((1-AMINOCYCLOPROPYL)METHOXY)-6-METHOXYQUINOLIN-4-YLOXY)-N-METHYL-1-NAPHTHAMIDE AND ITS CRYSTALLINE

(71) Applicant: Advenchen Pharmaceuticals, LLC, Moorpark, CA (US)

(72) Inventor: Guoqing Paul Chen, Westlake Village, CA (US)

(73) Assignee: Advenchen Pharmaceuticals, LLC, Moorpark, CA (US)

( * ) Notice: Subject to any disclaimer, the term of this patent is extended or adjusted under 35 U.S.C. 154(b) by 0 days.

(21) Appl. No.: 14/760,549

(22) PCT Filed: Jan. 17, 2014

(86) PCT No.: PCT/US2014/011948
§ 371 (c)(1),
(2) Date: Jul. 13, 2015

(87) PCT Pub. No.: WO2014/113616
PCT Pub. Date: Jul. 24, 2014

(65) Prior Publication Data
US 2015/0353496 A1    Dec. 10, 2015

Related U.S. Application Data

(60) Provisional application No. 61/754,516, filed on Jan. 18, 2013.

(51) Int. Cl.
| | |
|---|---|
| *C07D 215/233* | (2006.01) |
| *C07D 215/22* | (2006.01) |
| *C07C 271/24* | (2006.01) |
| *C07C 231/02* | (2006.01) |
| *C07C 269/00* | (2006.01) |
| *C07C 269/06* | (2006.01) |
| *C07C 303/26* | (2006.01) |
| *C07D 215/20* | (2006.01) |
| *C07C 309/66* | (2006.01) |

(52) U.S. Cl.
CPC .......... *C07D 215/22* (2013.01); *C07C 231/02* (2013.01); *C07C 269/00* (2013.01); *C07C 269/06* (2013.01); *C07C 271/24* (2013.01); *C07C 303/26* (2013.01); *C07C 309/66* (2013.01); *C07D 215/20* (2013.01); *C07D 215/233* (2013.01); *C07B 2200/13* (2013.01); *C07C 2101/02* (2013.01)

(58) Field of Classification Search
CPC .................................. C07D 215/233
USPC ....................................... 546/153
See application file for complete search history.

(56) References Cited

U.S. PATENT DOCUMENTS 8,163,923 B2 * 4/2012 Chen .................. C07D 215/233
546/159

* cited by examiner

*Primary Examiner* — Patricia L Morris

(57) ABSTRACT

The present invention relates a new process to synthesize 6-(7-((1-aminocyclo-propyl)-methoxy)-6-methoxyquinolin-4-yloxy)-N-methyl-1-naphthamide (AL3810) by deprotection of substituted benzyl 1-((6-methoxy-4-(5-(methylcarbamoyl)naphthalen-2-yloxy)quinolin-7-yloxy)-methyl)cyclopropylcarbamate (Formula I) under a diluted or weak acidic condition. A stable crystalline form of 6-(7-((1-aminocyclo-propyl)-methoxy)-6-methoxyquinolin-4-yloxy)-N-methyl-1-naphthamide has also been prepared.

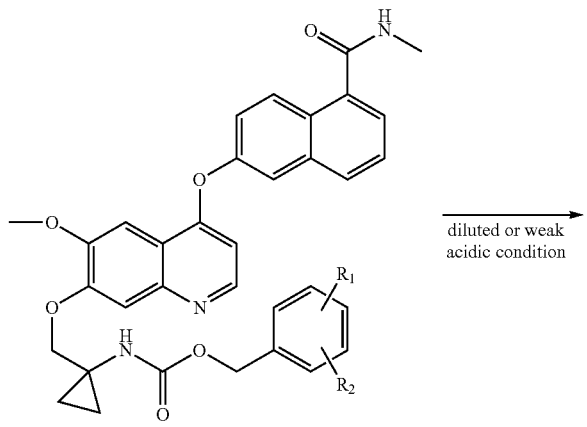

Formula I

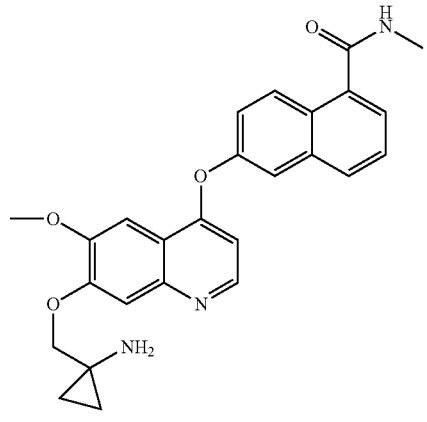

AL-3810

1 Claim, 4 Drawing Sheets

PROCESS FOR PREPARING THE ANTI-TUMOR AGENT 6-(7-((1-AMINOCYCLOPROPYL)METHOXY)-6-METHOXYQUINOLIN-4-YLOXY)-N-METHYL-1-NAPHTHAMIDE AND ITS CRYSTALLINE

This application claims the benefit of U.S. Provisional Applications 61/754,516 filed on Jan. 18, 2013

FIELD OF THE INVENTION

The present invention relates a new process to synthesize 6-(7-((1-aminocyclo-propyl)-methoxy)-6-methoxyquinolin-4-yloxy)-N-methyl-1-naphthamide (AL3810) by deprotection of substituted benzyl 1-((6-methoxy-4-(5-(methylcarbamoyl)naphthalen-2-yloxy)quinolin-7-yloxy)-methyl) cyclopropylcarbamate (Formula I) under a diluted or weak acidic condition. A stable crystalline form of 6-(7-((1-aminocyclo-propyl)-methoxy)-6-methoxyquinolin-4-yloxy)-N-methyl-1-naphthamide has also been prepared.

BACKGROUND OF THE INVENTION 6-(7-((1-Aminocyclopropyl)-methoxy)-6-methoxyquinolin-4-yloxy)-N-methyl-1-naphthamide (AL3810), or a pharmaceutically acceptable salt (such as hydrochloride salt) thereof, has been developed as an anti-tumor agent also named as E3810 and lucitanib, see "*Journal of Cellular and Molecular Medicine* vol. 16 issue 10 Oct. 2012. p. 2321-2330", "*Cancer Res* Feb. 15, 2011 vol. 71 no. 4 1396-1405".

This compound has been structurally disclosed in WO2008112408 as an agiogenesis inhibitor with few preparation methods. A new process has been disclosed in WO2010105761 with the removal of use of sodium azide. Both above disclosed processes have involved a deprotection of benzyl carbamate protected precursor by HBr/Acetic acid solution that is a strong, fuming and high corrosive acidic condition. No crystalline form has been disclosed.

SUMMARY OF THE INVENTION

Abbreviations

The following abbreviations are used and have the meaning below for ease of reference. EtOH: ethanol, MeOH: methanol, IPA: isopropanol, EtOAc: ethyl acetate, RT: room temperature, DIPEA: diisopropylethylamine, DCM: Dichloromethane, DMF: N,N-dimethylformamide, NMP: 1-Methyl-2-pyrrolidinone, ACN: acetonitrile, DEAD: Diethyl azodicarboxylate, DIAD: Diisopropyl azodicarboxylate, CDI: 1,1'-Carbonyldiimidazole, MeNH$_2$.HCl: methylamine hydrochloride, TSA.H2O: 4-toluensulfonic acid monohydrate, DMAP: 4-N,N-dimethylaminopyridine, MsCl: methanesulfonyl chloride, THF: tetrahydrofuran, TFA: trifluoroacetic acid, TEA: triethylamine, DPPA: diphenyl phosphoryl azide, eq: equivalent, g: gram, mg: milligram, ml: milliliter, min: minutes

Definitions

The term "halogen", as used herein, unless otherwise indicated, includes fluoro, chloro, bromo or iodo. such as fluoro and chloro.

The term "halogeno-C$_1$-C$_6$alkyl", as used herein, unless otherwise indicated, includes 1 to 6 halogen substituted alkyl, such as trifluoromethyl.

The term "C$_1$-C$_6$alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "C$_1$-C$_6$alkoxy", as used herein, unless otherwise indicated, includes —OC$_1$-C$_6$alkyl groups wherein C$_1$-C$_6$alkyl is as defined above, such as methoxy and ethoxy.

The term "cyano", as used herein, unless otherwise indicated, includes —C—N.

The term "nitro", as used herein, unless otherwise indicated, includes —NO$_2$.

Methods of Preparation

The present invention relates to a process for preparing 6-(7-((1-aminocyclopropyl)-methoxy)-6-methoxyquinolin-4-yloxy)-N-methyl-1-naphthamide (AL3810) by deprotection of substituted benzyl 1-((6-methoxy-4-(5-(methylcarbamoyl)naphthalen-2-yloxy)quinolin-7-yloxy)-methyl) cyclopropylcarbamate Formula I under a diluted or weak acidic condition according to Process A.

Process A

Scheme I

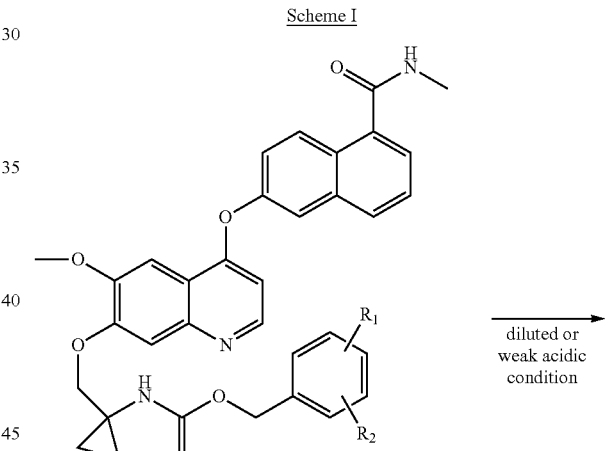

Formula I

AL-3810

Wherein
$R_1$ is selected from H, halogen, halogeno-$C_1$-$C_6$alkyl, $C_1$-$C_6$alkyl, $C_1$-$C_6$alkoxy, cyano or nitro;
$R_2$ is selected from $C_1$-$C_6$alkoxy, or nitro.

The present invention relates to the compound of Formula I.

The present invention relates to the methods of preparing a compound having the Formula I.

The present invention also relates to various intermediates useful in the preparation of a compound having the Formula I, and the present invention further relates to the methods of preparing such intermediates.

The present invention relates to the methods of preparing a crystalline form of 6-(7-((1-aminocyclopropyl)-methoxy)-6-methoxyquinolin-4-yloxy)-N-methyl-1-naphthamide.

DETAILED DESCRIPTION OF THE INVENTION

Figure 1:
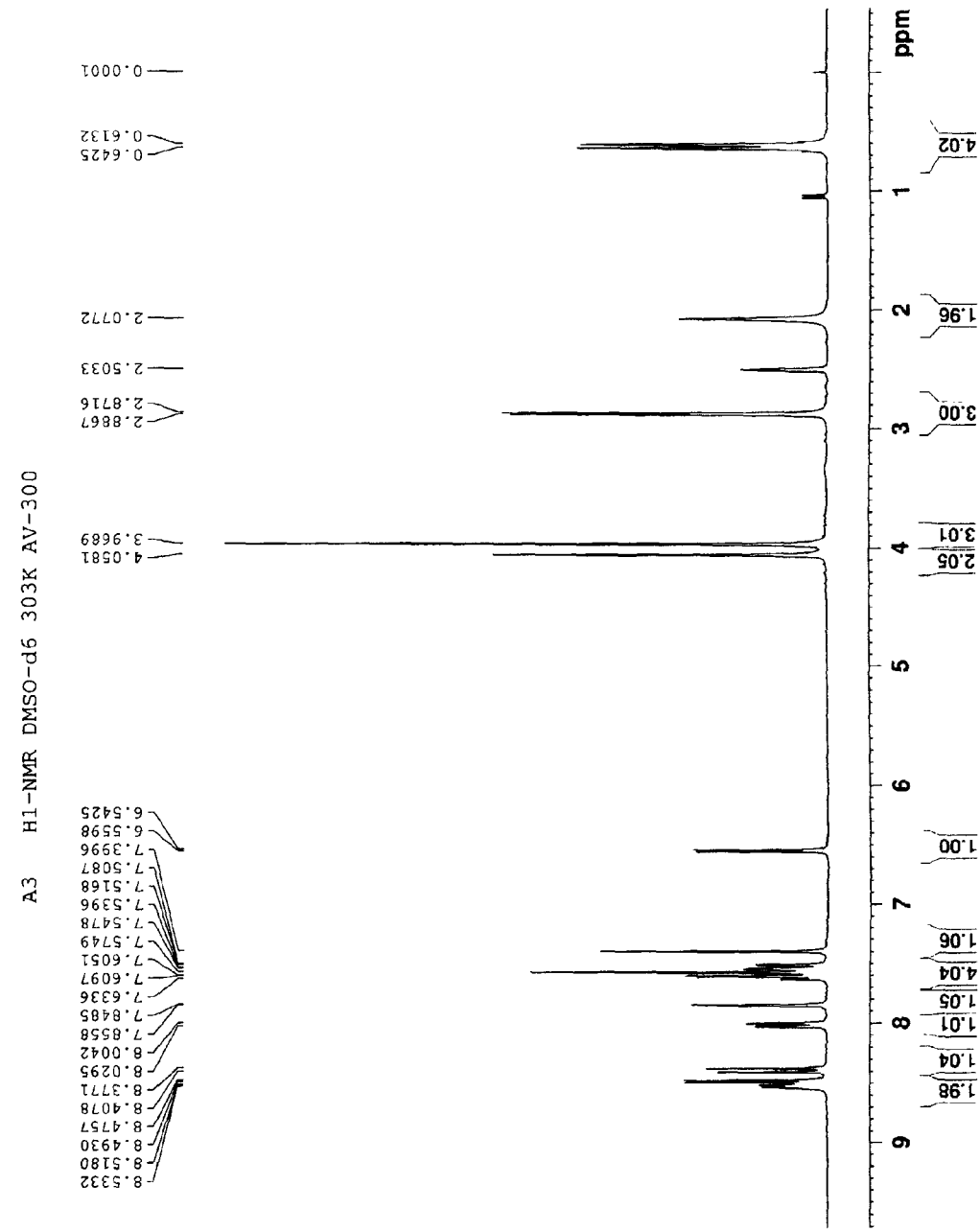
FIG. 1 provides a H1 nuclear magnetic resonance (NMR) graph of a crystalline form of 6-(7-((1-aminocyclopropyl)-methoxy)-6-methoxyquinolin-4-yloxy)-N-methyl-1-naphthamide.

The present invention relates to a process for preparing 6-(7-((1-aminocyclo-propyl)-methoxy)-6-methoxyquinolin-4-yloxy)-N-methyl-1-naphthamide (AL3810) by deprotection of substituted benzyl 1-((6-methoxy-4-(5-(methylcarbamoyl)naphthalen-2-yloxy)quinolin-7-yloxy)-methyl)cyclopropylcarbamate Formula I under a diluted or weak acidic condition according to above Process A.
Wherein
$R_1$ is selected from H, halogen, halogeno-$C_1$-$C_6$alkyl, $C_1$-$C_6$alkyl, $C_1$-$C_6$alkoxy, cyano or nitro; preferably selected from H, $C_1$-$C_6$alkoxy, or nitro;
$R_2$ is selected from $C_1$-$C_6$alkoxy, or nitro; preferably $R_2$ is methoxy.
A diluted or weak acidic condition is selected from 5-50% TFA in $CH_2Cl_2$ or $CH_3CN$, 10% HCl in ethanol, 4NHCl in dioxane, HCOOH in $CH_3CN$ or p-toluenesulfonic acid monohydrate in $CH_3CN$; preferably the acid is 10% TFA in $CH_2Cl_2$.

The total volume ratio of solvent to reactant is from 2 to 20 folds by weight. The reaction temperature is selected from 0 to 80° C. and the reaction time is selected from 0.5 to 24 hours.

A preferred procedure is shown in Scheme I.

The present invention relates to a process for preparing 6-(7-((1-aminocyclo-propyl)-methoxy)-6-methoxyquinolin-4-yloxy)-N-methyl-1-naphthamide (AL3810) by deprotection of 4-methoxybenzyl 1-((6-methoxy-4-(5-(methylcarbamoyl)naphthalen-2-yloxy)-quinolin-7-yloxy)-methyl)cyclopropylcarbamate Formula II according to Process B.

Process B

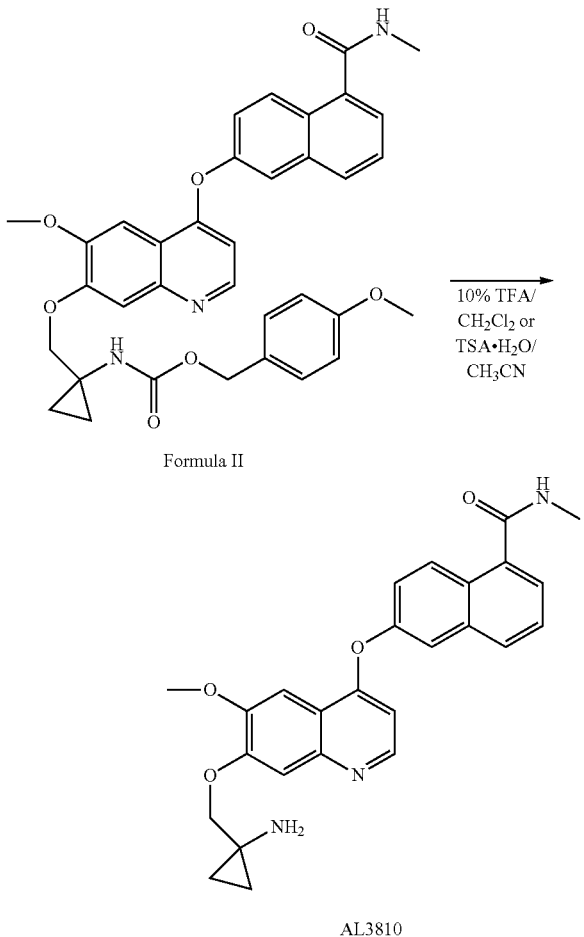

Scheme II

Formula II

AL3810

The present invention relates to the compound of Formula II.

The present invention relates to the methods of preparing a compound having the Formula II.

The present invention also relates to various intermediates useful in the preparation of a compound having the Formula II, and the present invention further relates to the methods of preparing such intermediates.

Process B of the invention comprises preparing AL3810, a preferred procedure is shown in Scheme II via:
(a) under a condition of 10% TFA in $CH_2Cl_2$, preferably at 0° C. to 50° C. for 3-10 hours with 5-20 folds volume of 10% TFA in $CH_2Cl_2$ as the solvent, or
(b) under a condition of 2-4 eq $TSA.H_2O$, preferably at room temperature to 80° C. for 10-24 hours with $CH_3CN$ as the solvent.

The present invention relates to a compound of Formula I or Formula II and the method preparing Formula I or Formula II according to Process C.

Process C

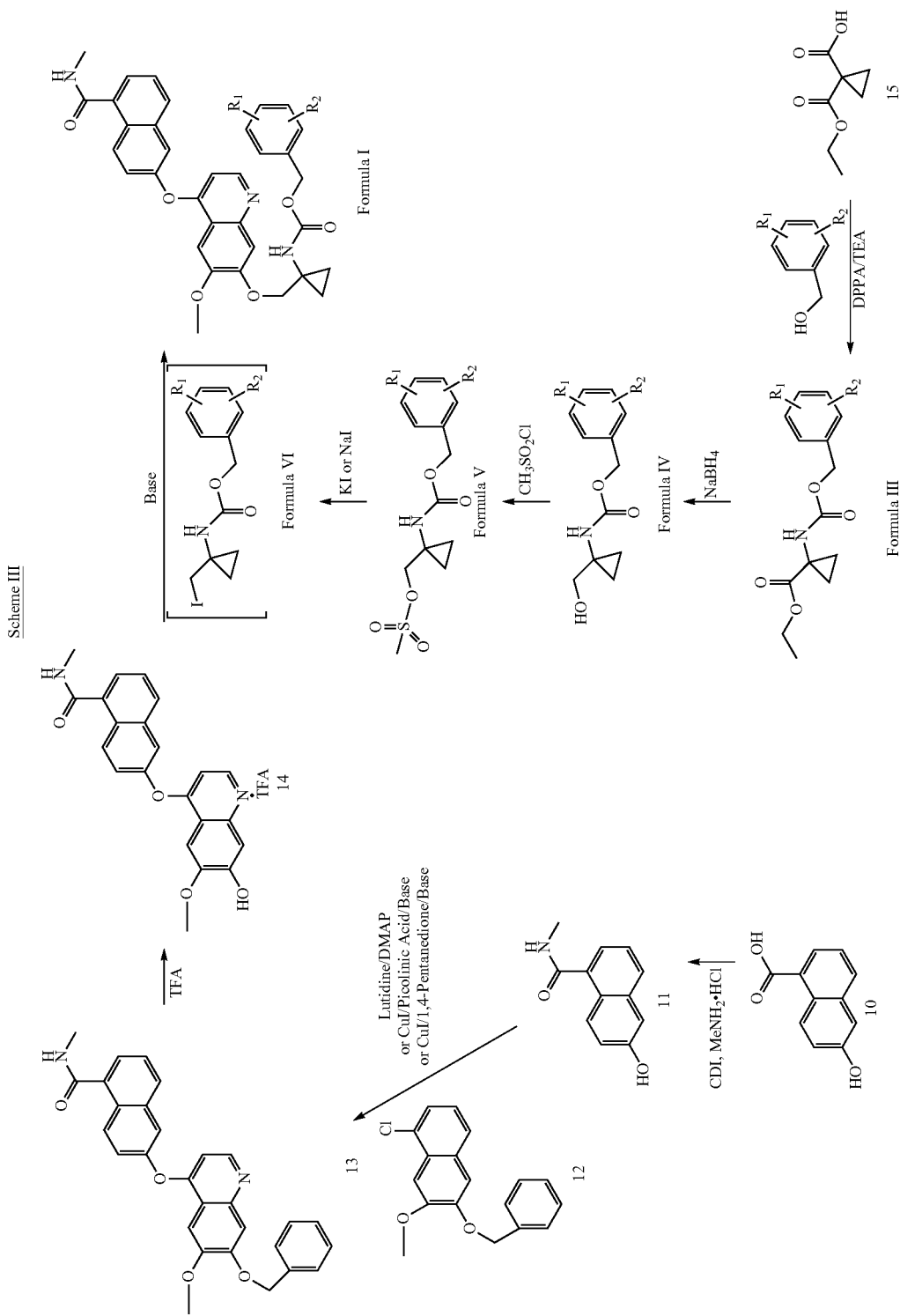

Scheme IV

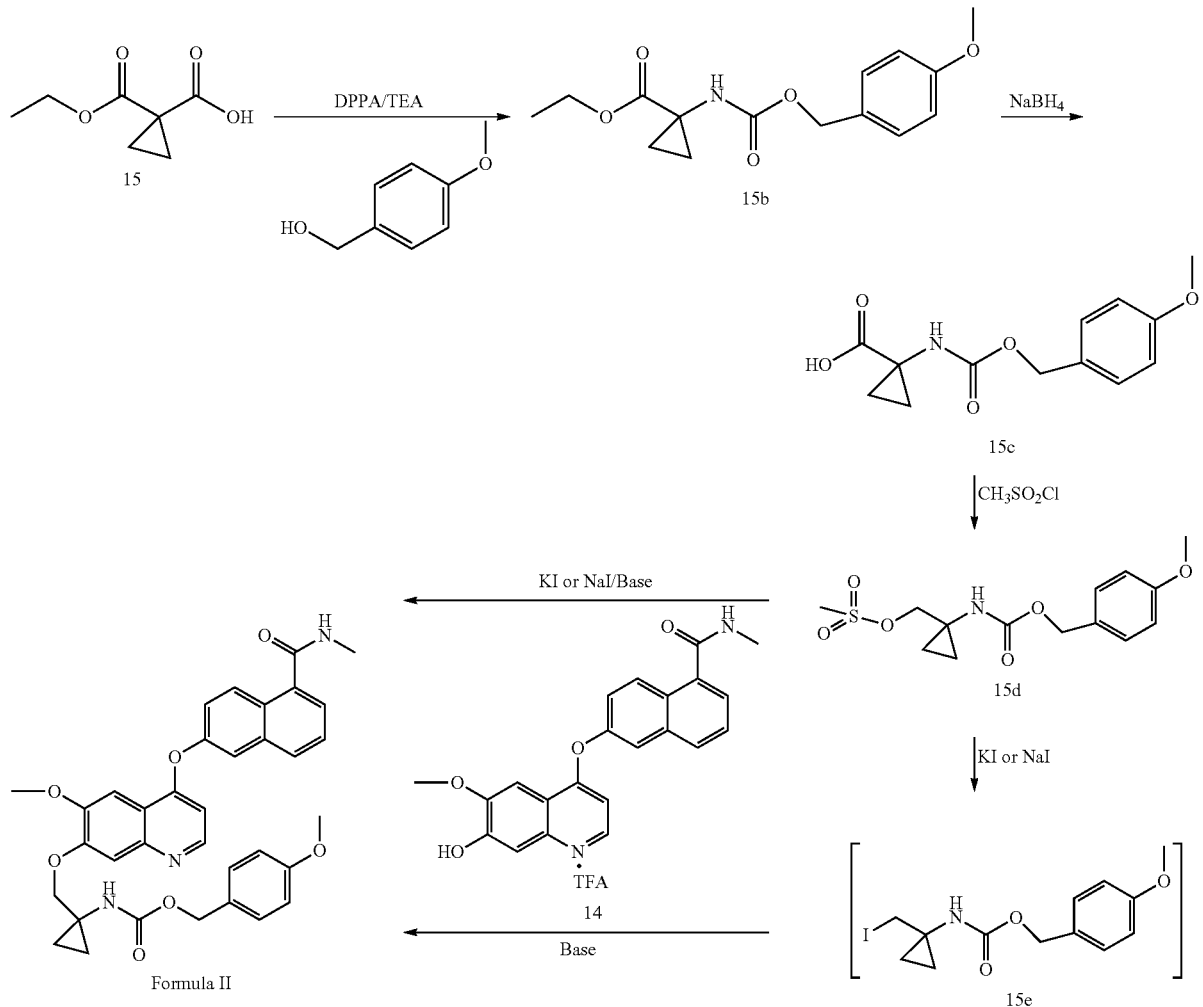

Wherein
R₁ is selected from H, halogen, halogeno-$C_1$-$C_6$alkyl, $C_1$-$C_6$alkyl, $C_1$-$C_6$alkoxy, cyano or nitro;
R₂ is selected from $C_1$-$C_6$alkoxy, or nitro.

Process C of the invention comprises preparing Formula I, a preferred procedure is shown in Scheme III via the reaction between formula 14 and Formula VI using a base, such as: $Na_2CO_3$, $Cs_2CO_3$ or $K_2CO_3$, or between formula 14 and Formula V using a base, such as: $Na_2CO_3$, $Cs_2CO_3$ or $K_2CO_3$, and KI or NAI to give Formula I, preferably the reaction is at a heated condition, such as 60-120° C. in acetone, DMF or NMP.

Formula 14 can be prepared by following steps:
(a) A direct acylation of formula 10 without any protection by methylamine hydrochloride with heat pre-activation of formula 10 at the presence of CDI gives formula 11, preferably the reaction is carried out in DMF or dioxane for 2-8 hours with 1.5-4 eq CDI at a heated condition, such as at 50-120° C.,
(b) (i) Coupling formula 11 with formula 12 (WO2008112408) at 100-160° C. in lutidine, such as 1,6-lutidine, or pyridine with 1.5-3 eq DMAP for 2-24 hours gives formula 13, or (ii) Coupling formula 11 with formula 12 under similar Ullmann reaction conditions, such as: a base, CuI and 2-picolinic acid gives formula 13, preferably a base is one of $Na_2CO_3$, $Cs_2CO_3$ and $K_2CO_3$, CuI amount is catalytic amount at 1-50% eq and 2-piclinic acid is at 1-50% eq. The reaction is at 100-160° C. in DMF or NMP for 10-36 hours, or (iii) Coupling formula 11 with formula 12 under similar Ullmann reaction conditions, such as: a base, CuI and pentanedione gives formula 13, preferably a base is one of $Na_2CO_3$, $Cs_2CO_3$ and $K_2CO_3$, CuI amount is catalytic amount at 1-50% eq and pentanedione is 1,4-pentanedione. The reaction is at 100-160° C. in DMF or NMP for 10-36 hours.
(c) Deprotecting formula 13 with TFA gives formula 14 as a TFA salt, preferably at 60-100° C. for 0.5-8 hours.

Formula VI or Formula V can be prepared by following steps:
(d) Reacting formula 15 with R₁, R₂ substituted benzyl alcohol with DPPA and triethylamine gives Formula III, preferably using 2-4 eq DPPA and 2-4 eq TEA in toluene or dioxane at a heated condition for 10-28 hours through Curtis rearrangement.

(e) Reducing Formula III by NaBH₄ gives Formula IV, preferably at reflux condition in THF with addition of methanol.
(f) Reacting Formula IV with CH₃SO₂Cl gives Formula V, preferably in a basic condition at −10° C.-25° C.
(g) Reacting Formula V with KI or NaI gives Formula VI, preferably refluxing in acetone or acetonitrile. This step can be modified as one pot reaction without isolation as Scheme III described.

Process C of the invention comprises preparing Formula II, a preferred procedure is shown in Scheme IV via the reaction between formula 14 and formula 15f using a base, such as: Na₂CO₃, Cs₂CO₃ or K₂CO₃, or between formula 14 and formula 15d using a base, such as: Na₂CO₃, Cs₂CO₃ or K₂CO₃, and KI or NaI at a heated condition, such as at 60-120° C. of one pot reaction in acetone, DMF or NMP to give Formula II.

The present invention relates to the compound of Formula I and the method preparing Formula I according to Process D.

Process D

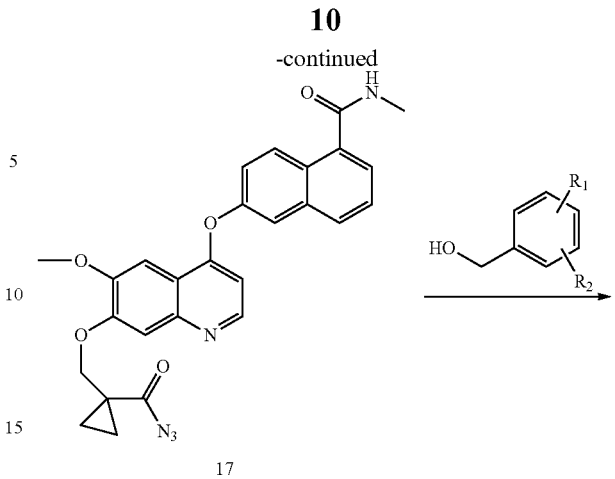

Process D of the invention comprises preparing Formula I, a preferred procedure is shown in Scheme V via acylazide formula 17 reacting with R₁, R₂ substituted benzyl alcohol in a heated condition, preferably toulene or dioxane refluxing condition.

Formula 17 can be prepared by reacting formula 16 with ethyl chloroformate at 0° C. in DMF or THF at the presence of TEA or DIPEA to form a mixed anhydride that can be reacted with NaN₃/DMF solution at similar temperature. Formula 16 can be prepared according to WO2008112408.

The present invention relates to the compound of Formula I and the method preparing Formula I according to Process E.

Process E

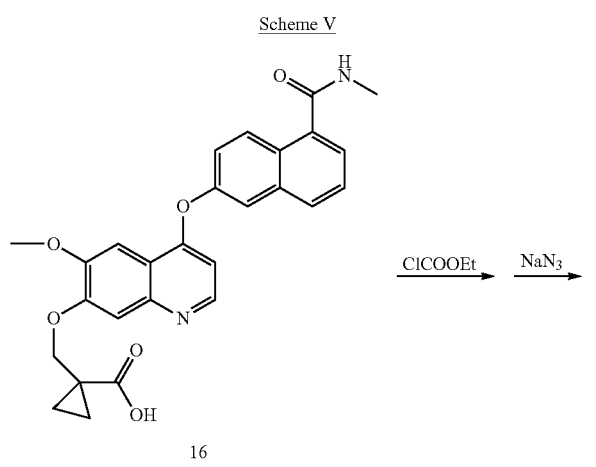

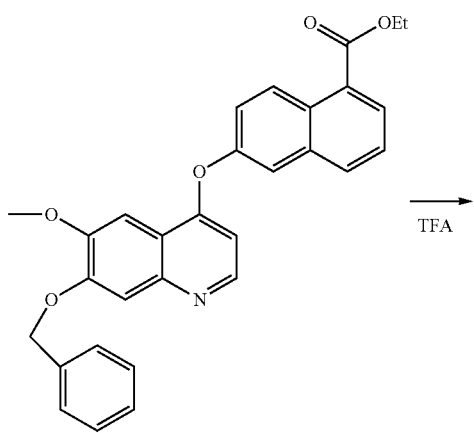

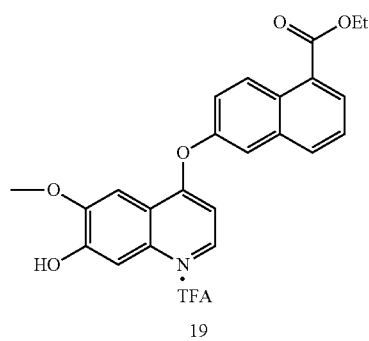

19

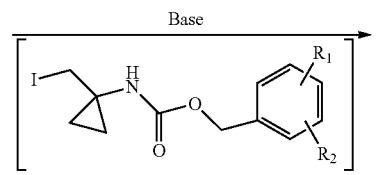

Formula VI

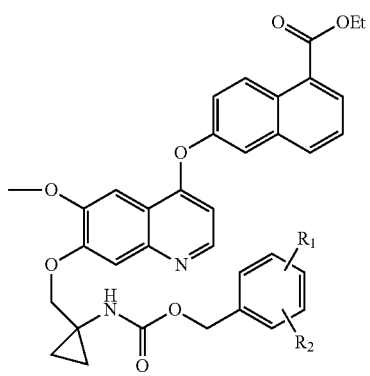

Formula VII

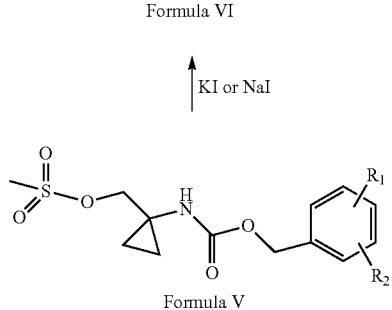

Formula V

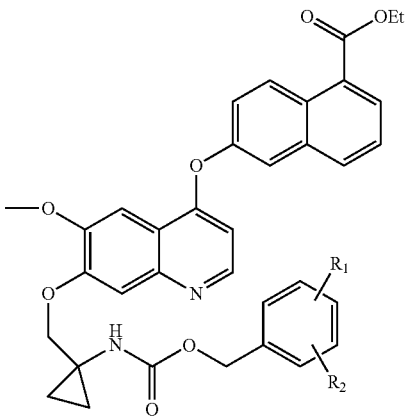

Formula VIII

Formula I ← CDI, MeNH$_2$•HCl

Wherein

R$_1$ is selected from H, halogen, halogeno-C$_1$-C$_6$alkyl, C$_1$-C$_6$alkyl, C$_1$-C$_6$alkoxy, cyano or nitro;

R$_2$ is selected from C$_1$-C$_6$alkoxy, or nitro.

Process E of the invention comprises preparing Formula I, a preferred procedure is shown in Scheme VI via acylation of Formula VIII with methylamine hydrochloride with heat pre-activation of formula VIII at the presence of CDI gives Formula I, preferably the reaction is carried out in DMF or dioxane for 2-8 hours with 1.5-4 eq CDI at 50-120° C. Formula VII can be similarly prepared by reacting formula 19 with Formula VI with a base, such as: Na$_2$CO$_3$, Cs$_2$CO$_3$ or K$_2$CO$_3$, or with Formula V in one pot KI or NaI with a base, such as: Na$_2$CO$_3$, Cs$_2$CO$_3$ or K$_2$CO$_3$, as described in Scheme III. Formula VIII can be prepared by hydrolysis of Formula VII under a strong basic condition, such as a mixture of an aqueous NaOH solution and EtOH. Formula 19 can be prepared according to WO2008112408 from formula 18.

The present invention relates to the compound of Formula I or Formula II and the method preparing Formula I or Formula II according to Process F.

Process F

Scheme VII

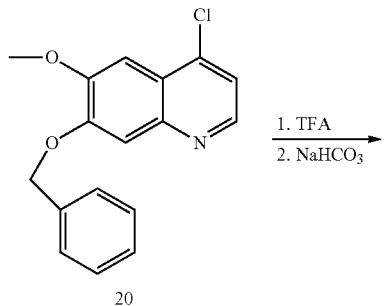

20

13
-continued

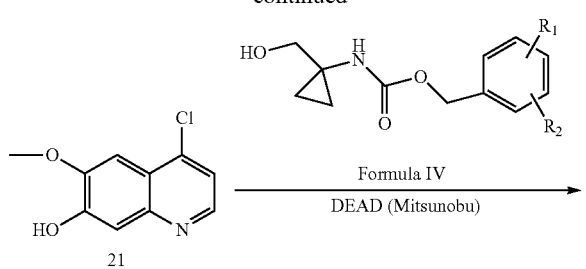

Formula IV
DEAD (Mitsunobu)

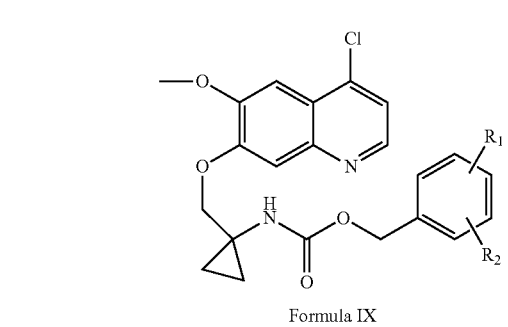

Formula IX

Lutidine/DMAP
or CuI/Picolinic Acid/Base
or CuI/Pentanedione/Base

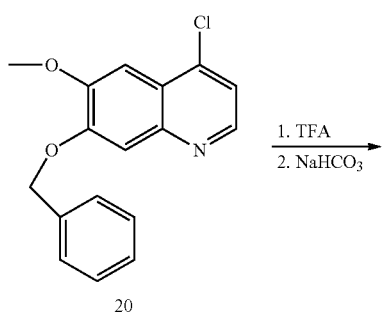

11

Formula I

Scheme VIII

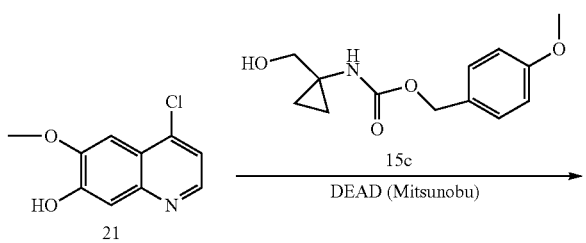

14
-continued

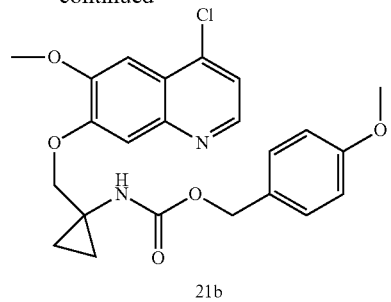

21b

Lutidine/DMAP
or CuI/Picolinic Acid/Base
or CuI/Pentanedione/Base

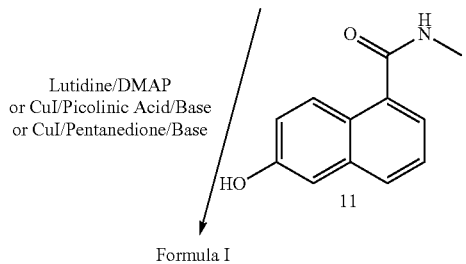

11

Formula I

Wherein $R_1$ is selected from H, halogen, halogeno-$C_1$-$C_6$alkyl, $C_1$-$C_6$alkyl, $C_1$-$C_6$alkoxy, cyano or nitro;

$R_2$ is selected from $C_1$-$C_6$alkoxy, or nitro.

Process F of the invention comprises preparing Formula I, a preferred procedure is shown in Scheme VII via:

(a) Coupling formula 11 with Formula IX at 100-160° C. in lutidine, such as 1,6-lutidine, or pyridine with 1.5-3 eq DMAP for 2-24 hours gives Formula I, or (b) coupling formula 11 with Formula IX under similar Ullmann reaction conditions, such as: a base of $Na_2CO_3$, $Cs_2CO_3$ and $K_2CO_3$ with catalytic amount of CuI (1-50% eq) and 2-piclinic acid (1-50% eq) at 100-160° C. in DMF or NMP for 10-36 hours gives Formula I, or (c) coupling formula 11 with Formula IX under similar Ullmann reaction conditions, such as: a base of $Na_2CO_3$, $Cs_2CO_3$ and $K_2CO_3$ with catalytic amount of CuI (1-50% eq) and pentanedione (1-50% eq), such as 1,4-pentanedione, at 100-160° C. in DMF or NMP for 10-36 hours gives Formula I.

Formula IX can be prepared by reacting Formula IV with formula 21 under Mitusnobu reaction condition in THF at 0-40° C. for 2-24 hours by use of Mitusnobu reagents, such as: DEAD or DIAD at the presence of a Mitsunobu ligand, such as triphenylphosphine. Formula 21 can be prepared by deprotection of formula 20 with TFA at 60-100° C. for 0.5-8 hours to give a TFA salt that can be neutralized by aqueous $NaHCO_3$ solution, and then filtered off.

Process F of the invention comprises preparing Formula II, a preferred procedure is shown in Scheme VIII via:

(a) Coupling formula 11 with formula 21b at 100-160° C. in lutidine, such as 1,6-lutidine, or pyridine with 1.5-3 eq DMAP for 2-24 hours gives Formula II, or (b) coupling formula 11 with formula 21b under similar Ullmann reaction conditions, such as: a base of $Na_2CO_3$, $Cs_2CO_3$ and $K_2CO_3$ with catalytic amount of CuI (1-50% eq) and 2-picolinic acid (1-50% eq) at 100-160° C. in DMF or NMP for 10-36 hours gives Formula II, or (c) coupling formula 11 with formula 21b under similar Ullmann reaction conditions, such as: a base of $Na_2CO_3$, $Cs_2CO_3$ and $K_2CO_3$ with catalytic amount of CuI (1-50% eq) and pentanedione (1-50% eq), such as 1,4-pentanedione, at 100-160° C. in DMF or NMP for 10-36 hours gives Formula II.

Formula 21b can be prepared by reacting formula 15c with formula 21 under Mitusnobu reaction condition in THF at 0-40° C. for 2-24 hours with use of Mitsunobu reagents, such as: DEAD or DIAD, at the presence of a Mitsunobu ligand, such as triphenylphosphine.

The present invention relates to the methods of preparing a crystalline form of 6-(7-((1-aminocyclopropyl)-methoxy)-6-methoxyquinolin-4-yloxy)-N-methyl-1-naphthamide (AL3810) by recrystallizing the crude product from isopropanol to give a stable crystalline form. The crude product was dissolved at refluxing condition for 15 minutes to 3 hours in isopropanol with certain amount of active carbon. The reaction was filtered at hot condition and cooled to room temperature (optionally cooled at 4° C.) for 4 to 48 hours. The precipitate was filtered and dried under high vacuum at 25° C.-80° C. to give a stable crystalline form with melting point at 185° C.-205° C. The crystalline form has no observable endotherm from about 40° C. to about 185° C. as determined by DSC. It has observable endotherm from about 185° C. to about 210° C. as determined by DSC. The crystalline form has a TGA thermogram that doesn't exhibit significant weight loss until at 210° C. to 250° C. to indicate that it is an unsolvated material. The crystalline form has 20-40 characteristic peaks on XRPD graph.

The following examples further illustrate the present invention, but should not construed as in any way to limit its scope.

Example 1

Representation of Process A and Process B

Process for preparation of 6-(7-((1-aminocyclopropyl)methoxy)-6-methoxy-quinolin-4-yloxy)-N-methyl-1-naphthamide (AL3810)

To a stirred mixture of 4-methoxybenzyl 1-((6-methoxy-4-(5-(methylcarbamoyl)-naphthalen-2-yloxy)-quinolin-7-yloxy)methyl)cyclopropylcarbamate Formula II (150 g) in DCM (1.5 L) was added TFA (150 ml) through an additional funnel for about 30 min at RT. The reaction was stirred at 30° C. for 4 hours and added into water (3 L). The aqueous layer was extracted with DCM twice (1.5 L×2) and basified with 3N NaOH (620 ml) to adjust pH 11-12 with a fine white solid precipitation. The solid was filtered and washed with water, further suction dry. The solid was dissolved into a mixture of chloroform/methanol (5 L, 3.5 L/1.5 L) and further washed with brine (2 L). It was dried with $MgSO_4$ and filtered. The solution was evaporated with EtOAc (2 L) three times to a slurry solution and cooled to RT. It was filtered and the filter cake was washed with ether, further air dried to give the crude titled compound 105 g, yield: 95.9%. MS: (M+1) 444.

Example 2

Representation of Process A and Process B

Process for preparation of 6-(7-((1-aminocyclopropyl)methoxy)-6-methoxy-quinolin-4-yloxy)-N-methyl-1-naphthamide (AL3810)

To a stirred mixture of 4-methoxybenzyl 1-((6-methoxy-4-(5-(methylcarbamoyl)naphthalen-2-yloxy)-quinolin-7-yloxy)methyl)cyclopropylcarbamate Formula II (1 g) in ACN (15 ml) was added $TSA.H_2O$ (3 eq). The reaction was stirred at RT for 24 hours and it was basified with 3N NaOH. The solution was extracted with DCM three times, washed with brine and dried with MgSO4. The solution then was filtered and evaporated, further recrystallized from IPA to give pure titled compound 550 mg, yield: 75%. MS: (M+1) 444.

Example 3

Representation of Process C

Process for preparation of 4-methoxybenzyl 1-((6-methoxy-4-(5-(methylcarbamoyl)-naphthalen-2-yloxy)-quinolin-7-yloxy)methyl)cyclopropylcarbamate Formula II

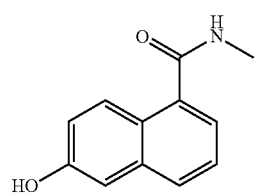

11

To a stirred mixture of 6-hydroxy-1-naphthoic acid (19 g, formula 10) in DMF (150 ml) was added CDI (22 g). The reaction was heated at 80° C. for 30 min and $CH_3NH_2.HCl$ (40 g) was added into the reaction. The reaction was heated for 3 hours at 80° C. and cooled to RT and further diluted with water (300 ml). It was acidified with 1N HCl to pH 2-3 and extracted three times with EtOAc (150 ml). The combined organic layer was washed with saturated $NaHCO_3$ solution followed by water and brine. The solution was dried with $Na_2SO_4$ and evaporated to give the 4-hydroxy-N-methyl-naphamide formula 11 compound 12 g.

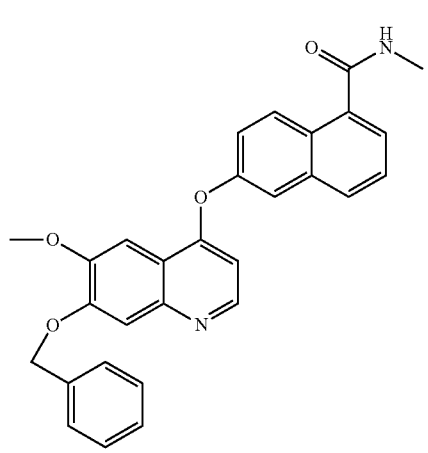

13

(i) To a mixture of formula 11 (6.5 g), formula 12 (6.5 g) and DMAP (5.5 g) was added 1,6-lutidine (20 ml). The reaction was stirred and heated at 135° C. for 5 hours from heterogeneous to homogeneous. The reaction was cooled and IPA (35 ml) was added into the reaction under slow stirring for 2 hours at RT. The solid was filtered and further washed with IPA, dried to give the formula 13 compound 5.8 g as a gray solid, yield 57%, or (ii) To a mixture of formula 11 (500 mg), formula 12 (500 mg), CuI (80 mg), Cs$_2$CO$_3$ (1 g) and 1-picolinic acid (150 mg) was added DMF (0.5 ml). The reaction was stirred and heated at 120° C. for 24 hours. It was directed loaded on silica gel column to purify to give the formula 13 compound 370 mg, yield 48%, or (iii) To a mixture of formula 11 (500 mg), formula 12 (500 mg), CuI (80 mg), Cs$_2$CO$_3$ (1 g) and 2,4-pentanedione (10 mg) was added DMF (0.5 ml). The reaction was stirred and heated at 120° C. for 24 hours. It was directed loaded on silica gel column to purify to give the formula 13 compound 450 ma, yield 58%.

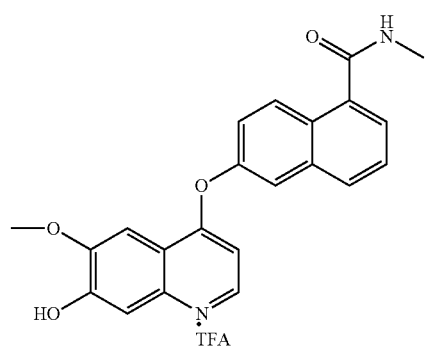

14

TFA

A mixture of formula 13 (5.8 g) and TFA (12 ml) was heated at 90° C. for one hour. The reaction was evaporated under reduced pressure and triturated with EtOAc. The solid was filtered and washed with EtOAc twice to give formula 14 as a TFA salt 5.5 g, yield 95%.

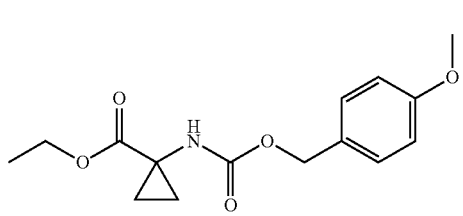

15b

To a mixture of acid-ester (8.2 g, formula 15) and 4-methoxybenzyl alcohol (9.5 g) in toluene (50 ml) was added DPPA (15 g), the reaction was stirred and TEA was added into the reaction through an additional funnel at RT. The reaction then was refluxed for 20 hours and cooled to RT. To the reaction was added 2N NaOH (30 ml) and followed by extraction with EtOAc three times. The combined organic layer was washed with water to neutral and dried with Na$_2$SO$_4$. The solution was filtered and evaporated followed by addition of EtOAc/PE (petroleum ether) and stored in a refrigerator overnight. The crystals were filtered and washed with cold EtOAc/PE to give an off white powder. The product formula 15b was vacuum oven dried at 30° C. to give 8.0 g as ethyl 1-((4-methoxybenzyloxy) carbonylamino)cyclopropanecarboxylate (formula 15b), yield: 53%. MS: (M+1) 294.

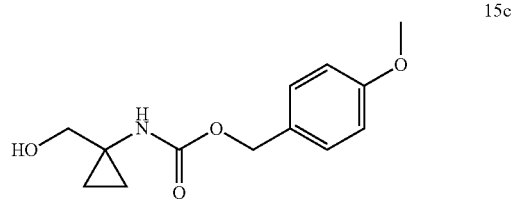 [SMILES: COc1ccc(COC(=O)NC2(CO)CC2)cc1]

15c

To a mixture of formula 15b (8.0 g) and THF (50 ml) was added NaBH$_4$ (8 g). The reaction was refluxed for 12 hours. Methanol (15 ml) was slowly added to the reaction and refluxed for 4 hour. The solvent was evaporated and cooled. NH$_4$Cl (6.3 g) and water (60 ml) were added and stirred. The mixture was extracted with DCM three times and dried with Na$_2$SO$_4$. The solution was filtered and evaporated followed by addition of ethanol to recrystallize overnight. The crystal was filtered to give an off white powder and further dried in oven to give the product 4.0 g as 4-methoxybenzyl 1-(hydroxymethyl)cyclopropylcarbamate (formula 15c), yield: 58%. MS: (M+1) 252.

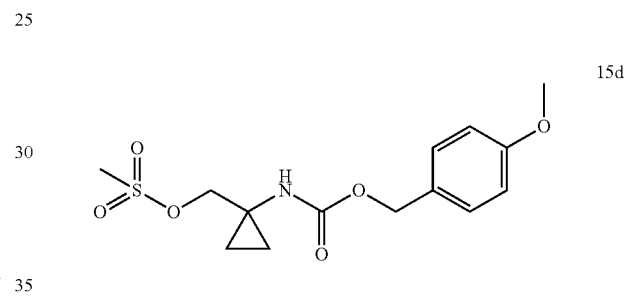

15d

To a stirred mixture of formula 15c (100 g) and DCM (400 ml) was added DIPEA (78 g). The result solution was cooled to 0-5° C. with ice/water and further stirred under this temperature for 15 min. MsCl (60 g) was added via an addition funnel dropwise keeping temperature below 5° C. for about 1.5 hours. After completion of addition, the reaction mixture was allowed stirring at 0-5° C. for 30 min and quenched with saturated NaHCO$_3$ (300 ml). The solution was extracted with 200 ml DCM twice. The combined DCM layer was washed with 0.1 N HCl (400 ml) followed by brine. It was dried over Na$_2$SO$_4$ and concentrated to obtain an off-white solid 123 g of formula 15d, MS: (M+1) 330.

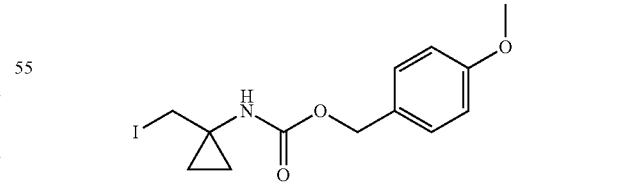

15e

To a stirred mixture of formula 15d (3.3 g) and KI (3.3 g) was added acetone (30 ml), the reaction was refluxed for 2 hours and cooled. The reaction was evaporated and extracted with EtOAc (30 ml) twice and washed with brine, further evaporated under reduced pressure to give the crude product 2.3 g of formula 15e, MS: (M+1) 362.

Formula II

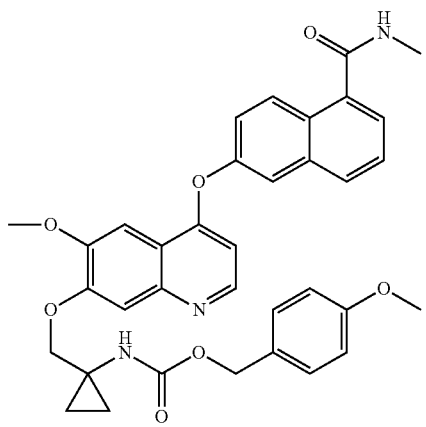

Method A:

To a stirred mixture of formula 14 (500 mg), formula 15d (450 mg), K$_2$CO$_3$ (400 mg) and NaI (180 mg) was added acetone (10 ml), the reaction suspension was heated to reflux for 20 hours as one pot reaction. The reaction was evaporated and purified on silica gel column to give the product 510 mg of Formula II. MS: (M+1) 608. $^1$H NMR (DMSO-d6): δ: 8.53-8.54 (m, 2H), 8.37-8.39 (d, 1H), 8.00-8.02 (d, 1H), 7.83-7.88 (m, 2H), 7.53-7.61 (m, 4H), 7.42 (s, 1H), 7.22-7.24 (d, 2H), 6.83-6.85 (d, 2H), 6.61-6.62 (d, 1H), 4.91 (s, 2H), 4.23 (s, 2H), 3.95 (s, 3H), 3.70 (s, 3H), 2.86-2.87 (d, 3H), 0.83-0.93 (d, 4H).

Method B:

To a stirred mixture of formula 14 (500 mg), formula 15e (500 mg) and K$_2$CO$_3$ (400 mg) was added acetone (10 ml), the reaction suspension was heated to reflux for 20 hours. The reaction was evaporated and purified on silica gel column to give the product 560 mg of Formula II. MS: (M+1) 608. $^1$H NMR conforms to Formula II from above Method A.

Method C:

To a stirred mixture of formula 14 (33 g), formula 15d (43 g), K$_2$CO$_3$ (41 g) and KI (16.6 g) was added acetone (400 ml). The reaction suspension was heated to reflux for about 30 hr. The reaction was concentrated and to the residue was added water (700 ml). The result suspension was stirred for 1 hour slowly to get a brown solid. The solid was filtered and rinsed with water twice further rinsed with ethanol. The crude product was dried in oven at 40° C. for 2-3 hours. The product was purified with IPA by recrystallization to give 29 g of Formula II. MS: (M+1) 608. $^1$H NMR conforms to Formula II from above Method A.

Example 4

Representation of Process D

Process for preparation of 4-methoxybenzyl 1-((6-methoxy-4-(5-(methylcarbamoyl)naphthalen-2-yloxy)-quinolin-7-yloxy)methyl)cyclopropyl-carbamate Formula II A mixture of 2-(1-((6-methoxy-4-(5-(methylcarbamoyl)naphthalen-2-yloxy)quino-lin-7-yloxy)methyl)cyclopropyl) acetyl azide formula 17 (WO2008112408, 150 mg) and 4-methoxybenzyl alcohol (0.15 ml) in toluene (10 ml) was refluxed for 1.5 hour. The reaction was evaporated and purified with silica gel column to give the titled product. Mass: (M+1), 608

Example 5

Representation of Process E

Process for preparation of 4-methoxybenzyl 1-((6-methoxy-4-(5-(methylcarbamoyl)naphthalen-2-yloxy)-quinolin-7-yloxy)methyl)cyclopropylcarbamate Formula II

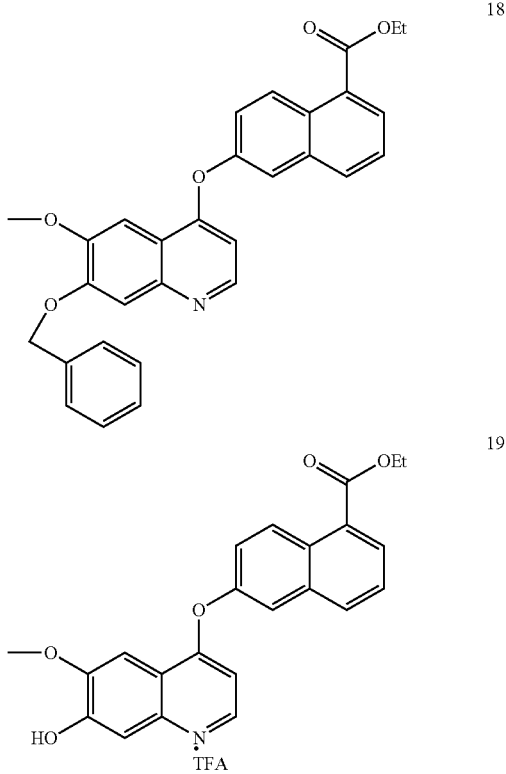

A mixture of 6-Hydroxy-1-naphthoic acid (1 g) and H$_2$SO$_4$ (0.2 ml) in EtOH (25 ml) was refluxed overnight and evaporated, followed by dissolving into EtOAc. The solution was washed with water, 1N NaHCO$_3$ solution and brine, further dried by Na$_2$SO$_4$. The solution was evaporated to give crude ethyl 6-hydroxy-1-naphthoate 0.9 g which was reacted with formula 12 at similar preparation conditions to formula 13 of Example 3 to give the above product of formula 18. Formula 19 was similarly prepared to formula 14 of Example 3.

A reaction between formula 19 and formula 15d similarly to the preparation of Formula II of Method A gave ethyl 6-(6-methoxy-7-((1-((4-methoxybenzyloxyl)carbonylamino)cyclopropyl)methoxy)quinolin-4-yloxy)-1-naphthoate which was hydrolyzed with 10% NaOH in EtOH at RT to give 6-(6-methoxy-7-((1-((4-methoxybenzyloxy)carbonylamino)cyclopropyl)methoxy)-quinolin-4-yloxy)-1-naphthoic acid. The resulting acid was acylated similarly to the preparation of formula 11 of Example 3 with CH$_3$NH$_2$.HCl under the heat pre-activation at the presence of CDI to give the titled product.

Example 6

Representation of Process F

Process for preparation of 4-methoxybenzyl 1-((6-methoxy-4-(5-(methylcarbamoyl)-naphthalen-2-yloxy)-quinolin-7-yloxy)methyl)cyclopropylcarbamate Formula II

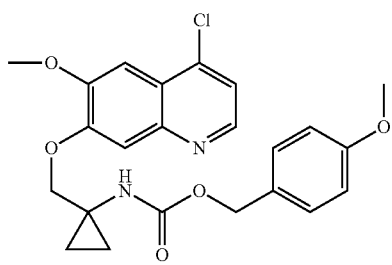

21b

To a mixture of 4-chloro-6-methoxyquilolin-7-ol (formula 21, 5.2 g), 1-((4-methoxybenzyloxy)carbonylamino) cyclopropanecarboxylate (formula 15b, 8.3 g) and triphenylphosphine (9.8 g) in THF (250 ml) was added DEAD (6.5 g) dropwise at RT in 1.5 hours, the reaction was further stirred for 20 hours at RT and evaporated. The residue was purified with silica gel column to give the 4-methoxybenzyl 1-((4-chloro-6-methoxy-quinolin-7-yloxy)methyl)cyclopropylcarbamate formula 21b product 6.5 g.

The titled compound of Formula II was then similarly prepared by using formula 21b to react with 4-hydroxy-N-methyl-naphamide formula 11 according to formula 13 of Example 3.

Example 7

Preparation of the crystalline form of 6-(7-((1-aminocyclopropyl)methoxy)-6-methoxy-quinolin-4-yloxy)-N-methyl-1-naphthamide (AL3810)

The crude product from Example 1 (105 g) was mixed with isopropanol (2.5 L) and active carbon (5 g), the mixture was heated to reflux for 0.5 hour to dissolve all crude product followed by filtration while it was hot, then the filtrate was refluxed again for 10 minutes and it was cooled to room temperature overnight under a slow stirring condition. The precipitate was filtered and washed with ethyl ether (500 ml×2), further dried under high vacuum at 80° C. to give the pure product (85 g) with melting point at 192° C.-196° C.

Figure 2:
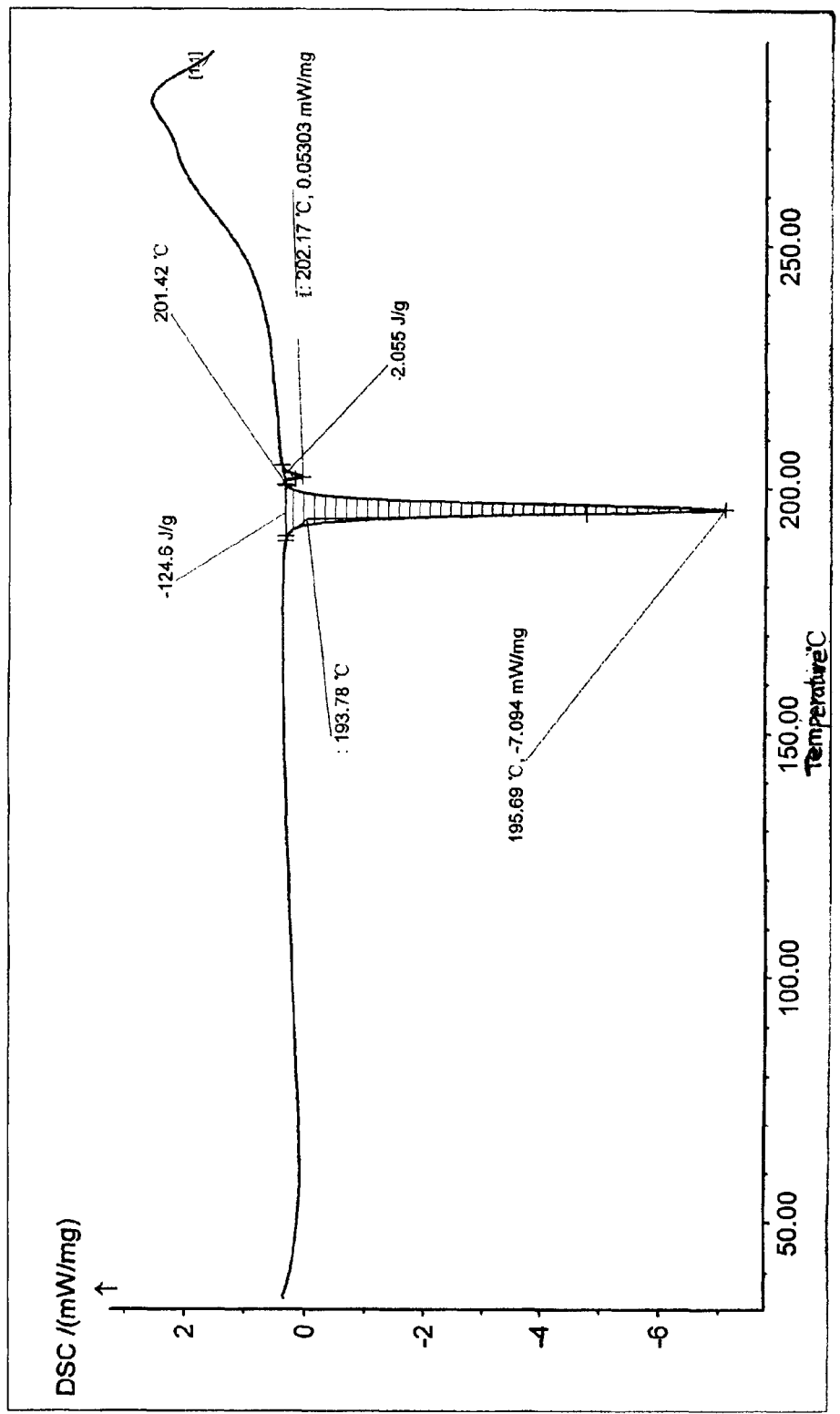
FIG. 2 provides a differential scanning calorimetric (DSC) graph of a crystalline form of 6-(7-((1-aminocyclopropyl)-methoxy)-6-methoxyquinolin-4-yloxy)-N-methyl-1-naphthamide.
Figure 3:
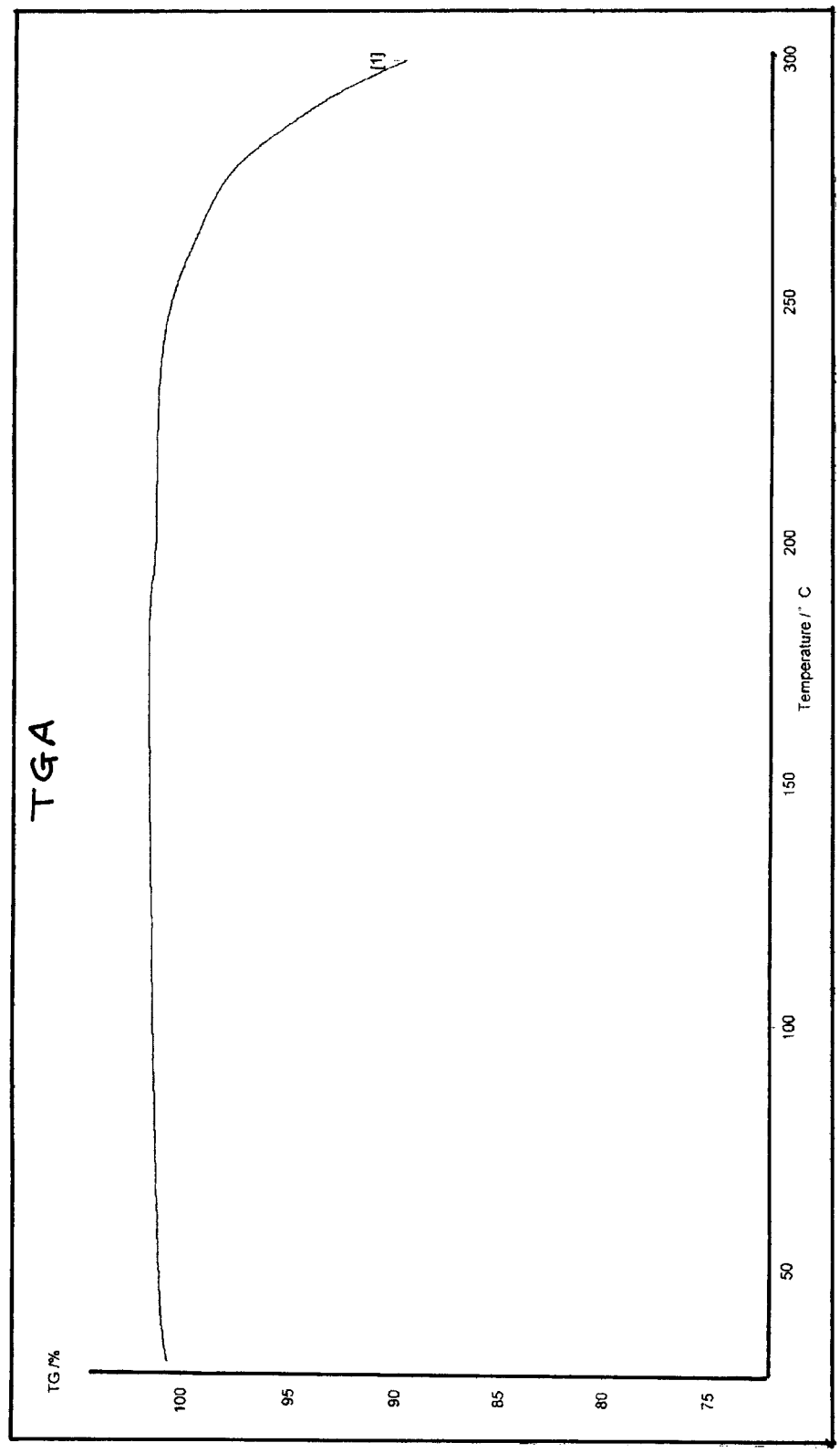
FIG. 3 provides a thermogravimetric analysis (TGA) graph of a crystalline form of 6-(7-((1-aminocyclopropyl)-methoxy)-6-methoxyquinolin-4-yloxy)-N-methyl-1-naphthamide.
Figure 4:
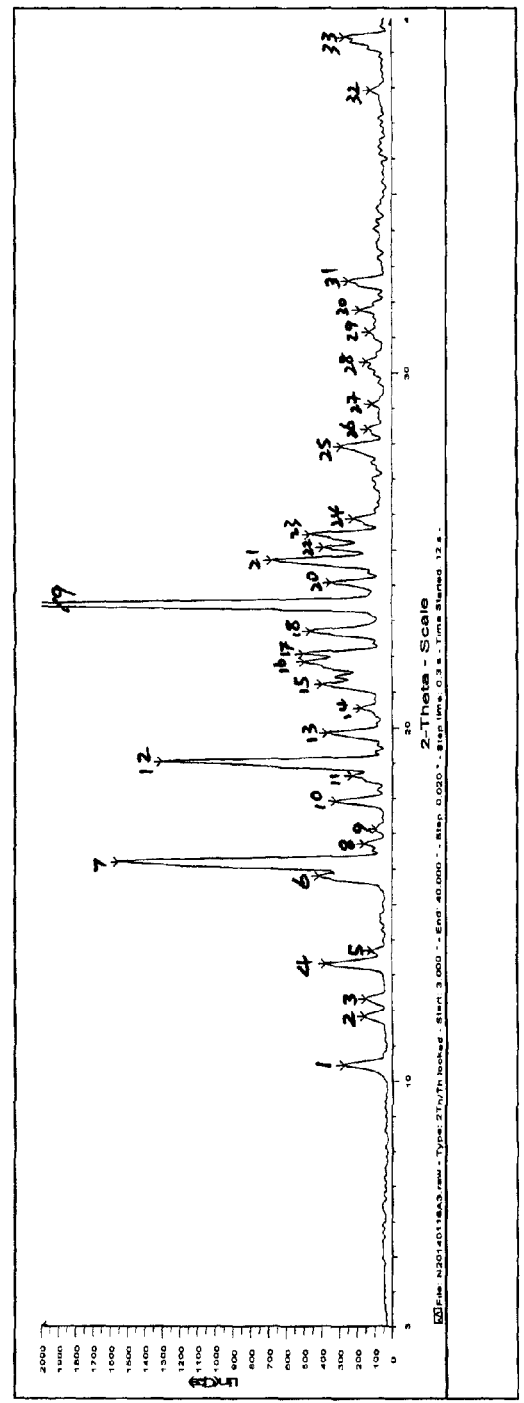
FIG. 4 provides an X-ray powder diffraction (XRPD) graph of a crystalline form of 6-(7-((1-aminocyclopropyl)-methoxy)-6-methoxyquinolin-4-yloxy)-N-methyl-1-naphthamide.

H1 NMR shown in FIG. 1.
DSC shown in FIG. 2 having observable endotherm from about 193° C.-202° C.
TGA shown in FIG. 3 demonstrating as an unsolvated material with weight loss at about 230° C.
XRPD shown in FIG. 4 having pattern compromising thirty three characteristic peaks with all intensity and intensity % expressed in d values and angles as follows:

| NO. | Angle | d value |
| --- | --- | --- |
| 1 | 10.429 | 8.476 |
| 2 | 11.811 | 7.487 |
| 3 | 12.287 | 7.198 |
| 4 | 13.293 | 6.655 |
| 5 | 13.658 | 6.478 |
| 6 | 15.778 | 5.612 |
| 7 | 16.186 | 5.472 |
| 8 | 16.682 | 5.310 |
| 9 | 17.102 | 5.181 |
| 10 | 17.907 | 4.949 |
| 11 | 18.631 | 4.759 |
| 12 | 19.027 | 4.661 |
| 13 | 19.847 | 4.470 |
| 14 | 20.545 | 4.320 |
| 15 | 21.214 | 4.185 |
| 16 | 21.843 | 4.066 |
| 17 | 22.058 | 4.026 |
| 18 | 22.682 | 3.917 |
| 19 | 23.453 | 3.790 |
| 20 | 24.065 | 3.695 |
| 21 | 24.708 | 3.600 |
| 22 | 25.072 | 3.549 |
| 23 | 25.435 | 3.499 |
| 24 | 25.886 | 3.439 |
| 25 | 27.929 | 3.192 |
| 26 | 28.420 | 3.138 |
| 27 | 29.137 | 3.062 |
| 28 | 30.331 | 2.944 |
| 29 | 31.172 | 2.867 |
| 30 | 31.803 | 2.811 |
| 31 | 32.613 | 2.743 |
| 32 | 37.959 | 2.369 |
| 33 | 39.470 | 2.281 |

And
H1 NMR shown in FIG. 1.
DSC shown in FIG. 2 having observable endotherm from about 193° C.-202° C.
TGA shown in FIG. 3 demonstrating as an unsolvated material with weight loss at about 230° C.
XRPD shown in FIG. 4 having pattern compromising characteristic peaks with intensity % greater than 10% expressed in d values and angles as follows:

| NO. | Angle | d value |
| --- | --- | --- |
| 1 | 10.429 | 8.476 |
| 4 | 13.293 | 6.655 |
| 6 | 15.778 | 5.612 |
| 7 | 16.186 | 5.472 |
| 10 | 17.907 | 4.949 |
| 12 | 19.027 | 4.661 |
| 13 | 19.847 | 4.470 |
| 15 | 21.214 | 4.185 |
| 16 | 21.843 | 4.066 |
| 17 | 22.058 | 4.026 |
| 18 | 22.682 | 3.917 |
| 19 | 23.453 | 3.790 |
| 20 | 24.065 | 3.695 |
| 21 | 24.708 | 3.600 |
| 22 | 25.072 | 3.549 |
| 23 | 25.435 | 3.499 |
| 25 | 27.929 | 3.192 |
| 31 | 32.613 | 2.743 |
| 33 | 39.470 | 2.281 |

What is claimed is:
1. A crystalline form of 6-(7-((1-aminocyclopropyl)methoxy)-6-methoxyquinolin-4-yloxy)-N-methyl-1-naphthamide exhibiting at least one of following properties:
a melting point at 192° C.-196° C.; a DSC having observable endotherm from about 193° C.-202° C.;

a TGA demonstrating as an unsolvated material with weight loss at about 230° C.;

a XRPD having pattern comprising characteristic peaks with all intensity % expressed in d values and angles or similar values and angles as follows:

| NO. | Angle | d value |
|---|---|---|
| 1 | 10.429 | 8.476 |
| 2 | 11.811 | 7.487 |
| 3 | 12.287 | 7.198 |
| 4 | 13.293 | 6.655 |
| 5 | 13.658 | 6.478 |
| 6 | 15.778 | 5.612 |
| 7 | 16.186 | 5.472 |
| 8 | 16.682 | 5.310 |
| 9 | 17.102 | 5.181 |
| 10 | 17.907 | 4.949 |
| 11 | 18.631 | 4.759 |
| 12 | 19.027 | 4.661 |
| 13 | 19.847 | 4.470 |
| 14 | 20.545 | 4.320 |
| 15 | 21.214 | 4.185 |
| 16 | 21.843 | 4.066 |
| 17 | 22.058 | 4.026 |
| 18 | 22.682 | 3.917 |
| 19 | 23.453 | 3.790 |
| 20 | 24.065 | 3.695 |
| 21 | 24.708 | 3.600 |
| 22 | 25.072 | 3.549 |
| 23 | 25.435 | 3.499 |
| 24 | 25.886 | 3.439 |
| 25 | 27.929 | 3.192 |
| 26 | 28.420 | 3.138 |
| 27 | 29.137 | 3.062 |
| 28 | 30.331 | 2.944 |
| 29 | 31.172 | 2.867 |
| 30 | 31.803 | 2.811 |
| 31 | 32.613 | 2.743 |
| 32 | 37.959 | 2.369 |
| 33 | 39.470 | 2.281. |

* * * * *